(12) United States Patent
Kubby

(10) Patent No.: US 10,105,343 B2
(45) Date of Patent: Oct. 23, 2018

(54) CANNABIS BASED COMPOSITIONS AND METHODS OF TREATING HYPERTENSION

(75) Inventor: Steven Wynn Kubby, South Lake Tahoe, CA (US)

(73) Assignee: KUBBY PATENT AND LICENSES, LIMITED LIABILITY COMPANY, Burnet, TX (US)

( * ) Notice: Subject to any disclaimer, the term of this patent is extended or adjusted under 35 U.S.C. 154(b) by 1427 days.

(21) Appl. No.: 12/772,140

(22) Filed: Apr. 30, 2010

(65) Prior Publication Data
US 2018/0104213 A1 Apr. 19, 2018

Related U.S. Application Data

(62) Division of application No. 12/772,132, filed on Apr. 30, 2010, now abandoned.

(51) Int. Cl.
*A61K 31/352* (2006.01)
*A61K 36/18* (2006.01)
*A61K 36/185* (2006.01)

(52) U.S. Cl.
CPC ............ *A61K 31/352* (2013.01); *A61K 36/18* (2013.01); *A61K 36/185* (2013.01)

(58) Field of Classification Search
CPC .................................................... A61K 36/00
USPC ....................................................... 424/725
See application file for complete search history.

(56) References Cited

U.S. PATENT DOCUMENTS

| 2,710,809 | A | * | 6/1955 | Andrews et al. | ............... | 426/93 |
| 6,630,507 | B1 | | 10/2003 | Hampson | | |
| PP27,475 | P2 | | 12/2016 | Kubby | | |
| 2007/0134399 | A1 | * | 6/2007 | Jarrett | ............... | 426/628 |

OTHER PUBLICATIONS

Brown, D. Cannabis: The Genus *Cannabis*; Overseas Publishers Association, NV, 2003, p. 42.*
Community Pharmacy; Aug. 1, 1998, 2 pages.*
Drake, J.: Grenadine Syrup From Pomegranates; Los Angeles Times, Los Angeles, CA, Sep. 8, 1998; 13 (2 pages printed from ProQuest Database).*
Lata et al. Thidiazuron-Induced High-Frequency Direct Shoot Organogenesis of Cannabis Sativa L.; In vitro Cellular & Developmental Biology; Jan./Feb. 2009; 45, 1; 8 pages.*
Lochner, T: Officials Tolerate Medical Marijuana Dispensary in Concord, Calif.; Knight Ridder Tribune Business news, May 7, 2005; 1, 2 pages.*
Rollitup.org Extracting THC With Coconut Oil; Online, URLhttp://www.rollitup.org/t/extracting-thc-with-coconut-oil.123332/ Oct. 23, 2008, 1 page post.*
US Newswire Vote Hemp: 'Marijuana Flavored' Lollipops Are Made With Cannabis Flower Essential Oil Not Hemp Seed Oil; Jun. 28, 2005; 1, 2 pages and.*
Akhavan, K, Marinol vs. Marijuana: Politics, Science, and Popular Culture, The American Alliance for Medical Cannabis, "Testimony before Congress, Lester Grinspoon, MD, of NORML." (1997).
California, Proposition 215, HS 11362.5 (a), "Compassionate Use Act of 1996 (Prop 215)".
Medical Use of Marijuana, Chapter 453A, Nevada, NRS 453a.
D. Kennedy et al., "Herbal Extracts and Phytochemicals: Plant Secondary Metabolites and the Enhancement of Human Brain Function", American Society for Nutrition, Adv. Nutr. 2, 2011, pp. 32-50.
Laboratory Testing of Steep Hill Halent, Cannabis Analytics and Research, testing Steven Kubby, Feb. 11, 2014.
"Ingredients Declared as Evaporated Cane Juice: Guidance for Industry", Office of Nutrition and Food Labeling and Standards Staff, HFS-820 Center for Food Safety and Applied Nutrition Food and Drug Administration, Apr. 35, 2016.
B. Wang et al., "Protective Effects of Wu-Zi-Yan-Zong-Fang on Amyloid β-induced Damage in In Vivo and In Vitro", The Pharmaceutical Society of Japan, Yakugaku Zasshi vol. 129, No. 8, 2009, pp. 941-948.
"Guidance for Industry Dissolution Testing of Immediate Release Solid Oral Dosage Forms", U.S. Department of Health and Human Services Food and Drug Administration Center for Drug Evaluation and Research (CDER), Aug. 1997.

* cited by examiner

*Primary Examiner* — Michael V Meller
(74) *Attorney, Agent, or Firm* — Jacobson, Holman, PLLC.

(57) ABSTRACT

The invention relates to a *Cannabis*-based pharmaceutical composition for the treatment of hypertensive disorders by submucosal delivery comprising a pharmaceutically acceptable base and an effective amount of at least one cannabinoid or endocannabinoid containing extract of a cloned hybrid of the plant *Cannabis sativa*, subspecies *sativa* and *Cannabis sativa*, subspecies *indica* of the CTSX-ISS lineage; and methods of treatment of primary and secondary hypertension, the secondary hypertension resulting from pheochromocytoma, primary hyperaldosteronism, adrenal hyperplasia, pulmonary hypertension, portal hypertension, folate deficiency hypertension, arterial hypertension or familial hypertension by administration between one and eight times per day.

5 Claims, No Drawings

CANNABIS BASED COMPOSITIONS AND METHODS OF TREATING HYPERTENSION

CROSS-REFERENCE TO RELATED APPLICATIONS

Not Applicable

STATEMENT REGARDING FEDERALLY SPONSORED RESEARCH OR DEVELOPMENT

Not Applicable

NAMES OF PARTIES TO A JOINT RESEARCH AGREEMENT

Not Applicable

REFERENCE TO SEQUENCE LISTING, A TABLE, OR A COMPUTER PROGRAM LISTING COMPACT DISK APPENDIX

Not Applicable

FIELD OF INVENTION

This invention relates to novel formulations to provide medical *Cannabis* effective in the treatment of hypertension, methods use of *Cannabis* in the treatment of hypertension, and process of manufacturing these compositions.

BACKGROUND

The present invention relates generally to compositions and methods for treating hypertension; more specifically, it relates to methods and compositions for treating or preventing hypertension whereby the many and varied problems associated with the disease can be prevented, arrested, substantially alleviated, or cured by the submucosal delivery of a pharmaceutically acceptable base and an effective amount of at least one cannabinoid- or endocannabinoid-containing extract of a cloned hybrid of the plant *Cannabis sativa*, subspecies *sativa* and *Cannabis sativa*, subspecies *indica* of the CTS-X-ISS lineage.

*Cannabis* boasts a long and pertinent history of medicinal use, based in the earliest known civilizations. The first recorded use of medical *cannabis* dates back to 2800 B.C., when the Chinese Emperor Shen-nung used it as a muscle relaxant and painkiller. The ancient Egyptians also found medical benefits in *cannabis*, as evidenced by their usage of it to quell the pangs of childbirth. Numerous other civilizations, including the Assyrians, Persians, Zulu, Spaniards, and countless others, have since established traditional medical applications of *cannabis*. Underlying this historical trend is the simple fact that the medical benefits of marijuana have, and continue to serve, numerous cultures.

In America, over one hundred articles recommending *cannabis* were published between 1840 and 1900 alone. *Cannabis* was among the handful of drugs listed in The Pure Food and Drug Act of 1906, effectuating the Agreement for Unification of Pharmacopeial Formulas for Potent Drugs (see Treaty Series 510, 1906), and was considered at the time to be the most daunting intrusion by federal authorities into interstate commerce. Although other federal agencies could regulate prices and occupational safety, the USDA then became engaged in the regulation of the very manufacture and sale of products, in addition to advertising. The Pure Food and Drug Act required only that certain specified drugs, including alcohol, cocaine, heroin, morphine, and *cannabis*, be accurately labeled with contents and dosage. Previously, many drugs had been sold as patent medicines with secret ingredients or misleading labels. Cocaine, heroin, *cannabis*, and other such drugs continued to be legally available without prescription as long as they were labeled. It is estimated that sale of patent medicines containing opiates decreased by 33% after labeling was mandated. Two subsequent laws, the Food, Drug, and Cosmetic Act of 1938 and the 1962 Kefauver-Harris Amendments, strengthened the 1906 act's legacy of empowering the FDA. Ironically, the Pure Food and Drug Act of 1906 is cited by drug policy reform advocates such as James P. Gray as a successful model for re-legalization of currently prohibited drugs by requiring accurate labels, monitoring of purity and dose, and consumer education.

*Cannabis* continued to play a prominent part of the pharmacopoeia from 1870 up until 1937, when the Marijuana Tax Act effectively banned the plant from public consumption regardless of intended use. Employed primarily as a painkiller during childbirth, as a treatment for asthma and gonorrhea symptoms, and as a relaxant for anxiety-prone patients, marijuana was formerly a well-documented drug in standard texts on pharmacology and therapeutics. When Congress first considered banning the *cannabis* plant, the respected American Medical Association (AMA) testified before federal committees in defense of marijuana's medical applicability. Despite the AMA's efforts, the political motivations behind outlawing the plant far outweighed any medical considerations, and in 1937, *cannabis* became illegal. The sudden and severe public reaction to this "new" drug was surprising, considering that no one in America had even heard the word "marijuana" until the late 1920s. Akhavan, K, Marinol vs. Marijuana: Politics, Science, and Popular Culture, The American Alliance for Medical *Cannabis* (1997).

While the medical use of marijuana has been well known for decades, it remained illegal based on its federal Class I scheduling until 1996 when California enacted Proposition 215, the first state law that permitted its medical use with a recommendation by a physician. Tetrahydrocannabinol (THC) alone does not provide the benefits of the other cannabinoids found in various strains; the limitations of formulations to a liquid or pill create difficulties for patients attempting to titrate the optimal dose for their various conditions.

Today, the benefits of *Cannabis* in a variety of medical conditions are so well established that they have been enacted into statute in fourteen states: Alaska, California, Colorado, Hawaii, Maine, Michigan, Montana, Nevada, New Jersey, New Mexico, Oregon, Rhode Island, Vermont and Washington. In California, *Cannabis* is deemed useful for cancer, anorexia, AIDS, chronic pain, spasticity, glaucoma, arthritis, migraine, or any other illness for which it provides relief. Section 11362.5 was added to the Health and Safety Code (b)(1)(A). In Nevada, NRS 453A.050 applies to a similar list of "Chronic or debilitating medical conditions" defined as 1)

Acquired immune deficiency syndrome; 2) Cancer; 3) Glaucoma; 4) A medical condition or treatment for a medical condition that produces, for a specific patient, one or more of the following: (a) Cachexia; (b) Persistent muscle spasms, including, without limitation, spasms caused by multiple sclerosis; c) Seizures, including, without limitation, seizures caused by epilepsy; (d) Severe nausea; or (e) Severe pain; or 5) Any other medical condition or treatment for a medical condition that is (a) Classified as a chronic or debilitating medical condition by regulation of the Division; or (b) Approved as a chronic or debilitating medical condition pursuant to a petition submitted in accordance with NRS 453A.710.

The etiology of glaucoma is an interruption to the normal outflow of aqueous humour within the chamber of the eye leading to elevated intra ocular pressure. As pressure rises, the optic nerve suffers irreversible damage, leading to a reduction in the field of vision and, ultimately, loss of eyesight. The most common type, chronic open-angle glaucoma, usually affects people over the age of 40, when the trabecular meshwork at the margins of the eye gradually becomes blocked and drainage slows. *Cannabis indica* and *sativa* have been used for many decades in glaucoma; for many patients is the only means to preserve their sight.

However, the benefits of *Cannabis* in other conditions associated with arteriolar constriction, though documented, are not as well known as in the case of glaucoma, some of the victims of which can find relief with no other medicine.

In an effort to provide the medical benefits of the plant, the drug dronabinol, Marinol®, a synthetic tetrahydrocannabinol (THC), once believed to be the active and therapeutic component of *Cannabis*, was introduced in 1985. Dronabinol is the subject of fourteen (14) patents, including use as an anti-emetic, U.S. Pat. No. 5,310,561, to Jao, et al, as an appetite stimulant, U.S. Pat. No. 6,703,418, to Plasse, and treatment for dementia, U.S. Pat. No. 5,804,592, to Volicer. U.S. Pat. No. 7,025,992, to Whittle discloses a *Cannabis*-based pharmaceutical formulation "for use in administration via a mucosal surface" which comprises both the cannabinoids cannabidiol (CBD) and tetrahydrocannabinol (THC), or the cannabinoids, tetrahydrocannabinovarin (THCV) and cannabidivarin (CBDV). The formulation is in a liquid dosage form producing particles having a mean aerodynamic particle size between 15 and 45 microns. Formulations suitable for oral administration can consist of (a) liquid solutions, such as an effective amount of *Cannabis* dissolved in diluents, such as water, oil, or saline, (b) capsules, sachets or tablets, each containing a predetermined amount of the active ingredient, as solids or granules, c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art. Whittle, however, does not disclose a hybrid cross of *Cannabis sativa*, ssp. *sativa* and C. s. ssp. *indica* of the CTSX-ISS lineage specifically developed for its anti-hypertensive properties.

Hampson, U.S. Pat. No. 6,630,507, of the United States Department of Health and Human Services, discloses cannabinoid derivatives that protect the brain from anoxic damage induced by the neuronal release of the neurotransmitter glutamate, which stimulates NMDA (N-methyl-D-aspartate), AMPA (.alpha.-amino-3-hydroxy-5-methyl-4-isoxazole propionate) and kainate receptors, and resultant calcium influx into the neurons and production of reactive oxygen species.

SUMMARY OF THE INVENTION

This inventor has discovered a means of providing the full panoply of cannabinoids in various strains, specifically of the CTSX-ISS lineage and most specifically the CTS-A plant described in contemporaneously filed plant application number, now patent PP27,475, incorporated by reference herein. This invention teaches a *Cannabis*-based pharmaceutical composition for the treatment of hypertensive disorders by submucosal delivery comprising a pharmaceutically acceptable base and an effective amount of at least one cannabinoid or endocannabinoid containing extract of a cloned hybrid of the plant *Cannabis sativa*, subspecies *sativa* and *Cannabis sativa*, subspecies *indica* of the CTSX-ISS lineage.

The other excipients in the lozenge enhance the stability of tetrahydrocannabinol and the other cannabinoids that are unstable when ingested alone. Most specifically, the lozenge utilizes the tricombs of the flower of the plant and the invention provides the process for producing the lozenge.

Also provided are methods of treating hypertensive disorders with the lozenge prepared from the extracts of tricombs of the *Cannabis* plant of the CTSX-ISS lineage.

DETAILED DESCRIPTION OF THE INVENTION

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

In the Summary above, the Description of the Invention, and the Claims and Abstract below, reference may be made to particular features (including method steps) of the invention. It is to be understood that this disclosure includes possible combinations of such particular features. For example, where a particular feature is disclosed in the context of a particular aspect or embodiment of the invention, or a particular claim, that feature may also be used, to the extent possible, in combination with and/or in the context of other particular aspects and embodiments of the invention, and in the invention generally.

The term "comprises" and grammatical equivalents thereof are used herein to mean that other components, ingredients, steps etc. are optionally present. For example, an article "comprising" (or "which comprises") components A, B and C can consist of (i.e. contain only) components A, B and C, or can contain not only components A, B and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

In this disclosure, where a range is given as "(a first number) to (a second number)" or "(a first number)-(a second number)", this means a range whose lower limit is the first number and whose upper limit is the second number. For example, 0-10 mm means a range whose lower limit is 0 mm, and whose upper limit is 10 mm.

The term "or" is used herein as a conjunction used to link alternatives in a series of alternatives. The term "and/or" is used herein as a conjunction meaning that either or both of two options may be valid.

In its first embodiment, this invention discloses a *Cannabis*-based pharmaceutical composition for the treatment of hypertensive disorders by submucosal delivery comprising a pharmaceutically acceptable base and an effective amount of at least one cannabinoid or endocannabinoid containing extract of a cloned hybrid of the plant *Cannabis sativa*, subspecies *sativa* and *Cannabis sativa*, subspecies *indica* of the CTSX-ISS lineage. A *Cannabis*-based pharmaceutical composition for the treatment of hypertensive disorders by submucosal delivery comprising a pharmaceutically acceptable base and an effective amount of at least one cannabinoid- or endocannabinoid-containing extract of a *Cannabis sativa* plant is most specifically provided as a lozenge. The hybrid may be, more specifically a *Cannabis sativa*, subspecies *sativa* and *Cannabis sativa*, subspecies *indica* of the CTSX-ISS lineage selected from CTSX-ISS lineage A; CTSX-ISS lineage B; AX-R, a cross between CTSX-ISS lineage A and a Romulin strain; AX-P, a cross between CTSX-ISS lineage A and a Pleadian strain. Most specifically, the composition for submucosal delivery is provided as a lozenge, and, most specifically, the extract of the cloned hybrid is an extract of the plant tricombs. Most specifically, it is CTS-A, described in contemporaneously filed plant patent, Application number now patent PP27,475.

In more specific embodiments, various dose ranges are provided. The plant *Cannabis sativa* of CTSX-ISS lineage may be present in an amount ranging from about 1 mg to about 1 gm, more specifically the extract of a cloned hybrid of the plant *Cannabis sativa* of CTSX-ISS lineage is present in an amount ranging from about 10 mg to about 150 mg, and most specifically the extract of a cloned hybrid of the plant *Cannabis sativa* of CTSX-ISS lineage is present in an amount of about 40 mg. The extract may be provided with an additional therapeutic agent, specifically an anti-inflammatory compound selected from the group consisting of a COX inhibitor, an eicosanoid, prostaglandin, a modulator of eicosanoid or prostaglandin production, or any eicosanoid receptor antagonist or agonist. Where the anti-inflammatory compound is included, the extract of a cloned hybrid of the plant *Cannabis sativa* of CTSX-ISS lineage is present in an amount ranging from about 10 mg to about 150 mg and the anti-inflammatory compound is present in an amount ranging from about 8 mg to about 800 mg.

Also disclosed are processes for the preparation of *cannabis* plant extracts containing cannabinolic acid in a pharmaceutically-acceptable base for submucosal delivery comprising the steps of: a) separating the tricomb-containing buds of *cannabis* plants from the remaining plant material; b) measuring a quantity of about 6 gm to about 8 gm buds; c) boiling the buds in about 90 cc to about 270 cc of coconut oil and about 800 to about 2500 cc of water for at about 4 to about 20 hours; d) removing the solid plant material by filtering the mixture through cheesecloth; e) recovering the coconut oil with resident tricombs from the aqueous layer; f) mixing the tricombs resident in said about 90 cc to about 270 cc coconut oil with about 0.6 cc sodium chloride; about 40 cc to about 200 cc of rice or corn syrup; about 50 cc to about 250 cc of water; about 200 cc to about 1 liter of a sugar or sugar alcohol; and about 2 gm to about 10 gm of lecithin; g) stirring said mixture constantly while bringing to a slow boil of about 114 degrees Celsius until all components are dissolved; h) continuing to boil until reaching hard crack temperatures of about 150 degrees Celsius to decarboxylate the said cannabinolic acid to active THC; i) removing mixture from heat less than 10 minutes after reaching hard crack; j) cooling the mixture to 140 degrees Celsius; k) pouring the mixture into forms; and l) allowing the mixture in the forms to cool to room temperature of about 23 degrees Celsius.

The process of may include an additional step of releasing the bubbles through mild agitation after said step (j) of cooling the mixture and prior to said step (k) of pouring the mixture into forms. The sugar or sugar alcohol may be, more specifically, selected from the group consisting of evaporated cane sugar, sucrose, and erythritol.

A more specific embodiment of the process comprises the same steps but utilizes a specific amount of each of the ingredients used: a) separating the tricomb-containing buds of *cannabis* plants from the remaining plant material; b) measuring a quantity of about 7 gm buds; c) boiling the buds in about 180 cc of coconut oil and about 1600 cc of water for at least 12 hours; d) removing the solid plant material by filtering the mixture through cheesecloth; e) recovering the coconut oil with resident tricombs from the aqueous layer; f) mixing the tricombs resident in said about 180 cc coconut oil with about 0.6 cc sodium chloride; about 80 cc of rice or corn syrup; about 120 cc of water; about 475 cc of evaporated cane juice, sucrose or erythritol; and about 3.6 gm of lecithin); g) stirring said mixture constantly while bringing to a slow boil of about 114 degrees Celsius until all components are dissolved; h) continuing to boil until reaching hard crack temperatures of about 150 degrees Celsius to decarboxylate the said cannabinolic acid to active THC; i) removing mixture from heat less than 10 minutes after reaching hard crack; j) cooling the mixture to 140 degrees Celsius; k) pouring the mixture into forms; and l) allowing the mixture in the forms to cool to room temperature of about 23 degrees Celsius. As in the first embodiment, the process may include the additional step of releasing the bubbles through mild agitation after said step (j) of cooling the mixture and prior to said step (k) of pouring the mixture into forms and the sugar or sugar alcohol may be, more specifically selected from the group consisting of evaporated cane sugar, sucrose, and erythritol.

When the anti-inflammatory is added to the lozenge in either of these embodiments, it is added after step (j) of cooling the mixture to avoid any cleavage of chemical bonds within the anti-inflammatory as a result of heating.

Also disclosed are methods of treating hypertension in a human by the administration of the *Cannabis*-based pharmaceutical composition comprising a pharmaceutically acceptable base and an effective amount of at least one cannabinoid or endocannabinoid containing extract of a cloned hybrid of the plant *Cannabis sativa*, subspecies *sativa* and *Cannabis sativa*, subspecies *indica* of the CTSX-ISS lineage by submucosal delivery. This method may be effectively used in essential hypertension or secondary hypertension, and, in more specific embodiments, the etiology of the secondary hypertension may be pheochromocytoma, primary hyperaldosteronism, adrenal hyperplasia, pulmonary hypertension, portal hypertension, folate deficiency hypertension, arterial hypertension or familial hypertension. More specifically, the administration is in the form of at least one lozenge placed in a position selected for on the superior surface of the tongue, inferior to the tongue, or on the mucosal surface of the cheek of a human in need thereof between one and eight four times per day. Most specifically, one lozenge is placed in a position selected for on the superior surface of the tongue, inferior to the tongue, or on the mucosal surface of the cheek of a human in need thereof about four times per day.

EXAMPLE

The following non-limiting example demonstrate the usefulness of this method of administering medical *cannabis* to patients in need thereof:

In 1999, this inventor's doctors told him that after completing extensive medical tests at the University of Southern California's School of Medicine his prognosis was poor. According to Dr. Vincent DeQuattro, a USC professor and world authority on adrenal cancer, his blood contained deadly levels of adrenaline, more than enough to kill anyone else.

Nearly everyone else who has ever had the malignant form of the inventor's disease has died within a few years. The inventor credits his survival, now 35 years since his diagnosis, to medical marijuana, something DeQuattro considered a "medical miracle." Dr. DeQuattro has written that the inventor could suffer a heart attack or stroke if deprived of marijuana and that no other form of therapy is available.

Despite the seriousness and dramatic dangers of his disease, Mr. Kubby was arrested and jailed for using the only medicine that worked for him. During his first few days of incarceration, he experienced excruciating pain, a vicious high blood-pressure crisis, passed blood in his urine and over a period of 60 days, and lost 33 pounds. However, thanks to the efforts of nearly a hundred demonstrators and massive media coverage, the Placer County Jail staff became painfully aware of the situation and acted decisively to make sure he had proper medical care. To everyone's relief, we learned that Marinol is an acceptable, if not ideal, substitute for whole *cannabis* in treating the inventor's otherwise fatal disease.

The fact that Marinol, which is pure THC, was extremely effective in controlling his hypertension was great, but it left the inventor with constant nausea. That's when he started to experiment with lozenges to see if he could create a natural *cannabis* based lozenge that would control hypertension, without undesirable side effects.

This led the Inventor to the development that is taught in this invention. Fortunately, the lozenge developed was found it to be the ideal solution for delivering cannabinoids into his body, and he shared it with other medical *cannabis* patients.

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A process for the preparation of *cannabis* extracts of a hybrid of *Cannabis sativa* and *Cannabis indica*, subspecies *indica*, consisting essentially of the steps of:
   a. separating trichome of *cannabis* of a hybrid of *Cannabis sativa* and *Cannabis indica*, subspecies *indica*;
   b. measuring a quantity of about 6 gm to about 8 gm of the buds of *cannabis*;
   c. boiling the buds of *cannabis* in about 90 cc to about 270 cc of coconut oil and about 800 to about 2500 cc of water for about 4 to about 20 hours to yield a solid *cannabis* mixture;
   d. removing the solid *cannabis* mixture by filtering the solid *cannabis* mixture through cheesecloth;
   e. separating and recovering out the about 90 cc to about 270 cc of coconut oil with trichomes within it from the aqueous layer of the solid *cannabis* mixture;
   f. admixing the about 90 cc to about 270 cc coconut oil with tricornes within it with about 0.6 cc sodium chloride; about 40 cc to about 200 cc of rice or corn syrup; about 50 cc to about 250 cc of water; about 200 cc to about 1 liter of a sugar or sugar alcohol; and about 2 gm to about 10 gm of lechithin to form a *cannabis* mixture;
   g. stirring said *cannabis* mixture constantly while bringing to a slow boil of about 114° C. until all components in the *cannabis* mixture are dissolved;
   h. continuing to boil the *cannabis* mixture until reaching a hare crack temperature of about 150° C. to decarboxylate the cannabinolic acid in the *cannabis* mixture to active the THC within the *cannabis* mixture;
   i. removing the *cannabis* mixture from the heat after 10 minutes after reaching hard crack;
   j. cooling the *cannabis* mixture to 140° C. until bubbles form within it;
   k. agitating the *cannabis* mixture mildly to release the bubbles within it;
   l. pouring the *cannabis* mixture into forms;
   m. allowing the *cannabis* mixture in the forms to cool to room temperature of about 23° C. to yield *cannabis* extracts of a hybrid of *Cannabis sativa* and *Cannabis indica*, subspecies *indica*.

2. The process of claim 1, further consisting essentially of the additional step of releasing the bubbles through mild agitation after said step (j) of cooling the mixture and prior to said step (k) of pouring the mixture into forms.

3. The process of claim 2, wherein said sugar or sugar alcohol is selected from the group consisting of evaporated cane juice sugar, sucrose, and erythritol.

4. The process of claim 3, further consisting essentially of the additional step of releasing the bubbles through mild agitation after said step (j) of cooling the mixture and prior to said step (k) of pouring the mixture into forms.

5. The process of claim 2, wherein said sugar or sugar alcohol is cane sugar.

* * * * *